United States Patent [19]

Tateosian et al.

[11] Patent Number: 4,698,373

[45] Date of Patent: * Oct. 6, 1987

[54] STABLE ONE PART DENTAL COMPOSITIONS EMPLOYING IPN TECHNOLOGY

[75] Inventors: Louis Tateosian, York, Pa.; Frederick D. Roemer, Bloomington, Ind.

[73] Assignee: Dentsply Research & Development Corp., Milford, Del.

[*] Notice: The portion of the term of this patent subsequent to Aug. 2, 2000 has been disclaimed.

[21] Appl. No.: 605,629

[22] Filed: Apr. 30, 1984

Related U.S. Application Data

[63] Continuation of Ser. No. 227,138, Jan. 21, 1981, abandoned, which is a continuation-in-part of Ser. No. 8,507, Feb. 1, 1979, abandoned.

[51] Int. Cl.$^4$ .................. C08F 2/50; C08F 257/00; C08F 261/00; A61C 13/01
[52] U.S. Cl. .................................... 522/95; 264/22; 264/17; 522/10; 522/102; 522/110; 523/115; 525/193; 525/217
[58] Field of Search .................. 204/159.16; 522/9.5, 522/102, 110

[56] References Cited

U.S. PATENT DOCUMENTS

| | | | |
|---|---|---|---|
| 3,427,274 | 2/1969 | Cornell | 260/31.8 |
| 3,470,615 | 10/1969 | Petner | 264/19 |
| 4,076,671 | 2/1978 | Bright | 428/451 |
| 4,302,376 | 11/1981 | Walkowiak | 525/226 |
| 4,308,190 | 12/1981 | Walkowiak | 525/226 |
| 4,369,262 | 1/1983 | Walkowiak | 523/109 |
| 4,396,377 | 8/1983 | Roemer et al. | 523/115 |
| 4,396,476 | 8/1983 | Roemer et al. | 204/159.16 |
| 4,433,958 | 2/1984 | Fellman et al. | 523/115 |

FOREIGN PATENT DOCUMENTS

| | | |
|---|---|---|
| 511802 | 4/1955 | Canada . |
| 569975 | 6/1945 | United Kingdom . |

*Primary Examiner*—John C. Bleutge
*Assistant Examiner*—Arthur H. Koeckert
*Attorney, Agent, or Firm*—Woodcock Washburn Kurtz Mackiewicz & Norris

[57] ABSTRACT

Compositions hardenable by exposure to heat or electromagnetic radiation are provided by dissolving together to form a blend from about 0% to about 50% by weight of an uncrosslinked polymer, from about 2% to about 30% of a polymerizable monomer, from about 10% to about 70% of a crosslinked polymer in the form of discrete particles having average diameters of from 0.001 micron to about 500 microns and being swollen in said solution and from about 20% to about 70% of a crosslinking agent for said monomer. Such compositions exhibit superior chemical and physical characteristics when hardened and are suitable in a wide variety of applications as construction media. Such compositions are especially suitable in the production of prosthetic dental appliances, such as, for example, prosthetic teeth. It is believed that the hardening of such compositions as, for example, during the preparation of dental appliances forms a polymer system known as an interpenetrating polymer network.

32 Claims, No Drawings

STABLE ONE PART DENTAL COMPOSITIONS EMPLOYING IPN TECHNOLOGY

CROSS REFERENCE TO RELATED APPLICATIONS

This is a continuation of application Ser. No. 227,138, filed 1/21/81, which is a continuation in part of Ser. No. 008,507 filed Feb. 1, 1979, both now abandoned.

BACKGROUND OF THE INVENTION

This invention provides hardenable compositions useful as construction media for a wide range of applications. Particular utility is found in the dental and medical arts where such compositions are highly suitable for the formation and construction of artificial teeth and for other dental and prosthetic uses. More particularly, the invention relates to polymeric compositions comprising crosslinked polymers, monomers, and crosslinking agents for said monomers, and optionally uncrosslinked polymers which form precursor blends. These precursor blends are capable of being formed or molded and caused to polymerize to provide articles possessing superior physical and physiochemical properties.

Artificial teeth should exhibit certain physical and physiochemical characteristics to be suitable for use. They should be hard and resistant to chipping, durable, and stable to solvents, water, and heat. In addition, they should be of an aesthetically acceptable color, i.e., close to that of natural teeth, or be amenable to artificial coloration. The teeth should not cause excessive wear to opposing natural or artificial teeth, should not wear out of occlusion, and should be capable of being bonded firmly to supportive structures. They should also be amenable to ordinary means of physical shaping, grinding, and polishing, so as to minimize production costs.

Various metals and ceramics have been traditionally used for the formation of artificial teeth and other dental appliances. These, however, possess certain inherent deficiencies which lessen their desirability in dental applications. Thus, the metallic color of gold, amalgam, and other metallic species serves as an aesthetic detraction to the wearer of appliances made therefrom. In addition, the high cost of most noble metals from which many such appliances are commonly made leads to a cost consideration whenever their use is contemplated. Ceramic materials, another common alternative, are often difficult to form into acceptable shapes, and may tend to evidence abrasive and aesthetically unpleasant subsurfaces upon the physical wearing-away of surface layers. Such materials are also difficult to polish satisfactorily. These reasons together with factors related to cost, to consumer preference, to the technical skills of dental practitioners, and to convenience have motivated a search for alternative compositions suitable for the construction of dental appliances, especially artificial teeth.

Of the presently available organic compositions used for the construction of artificial teeth, most are composed of acrylics, often crosslinked by polyfunctional moieties. While such compositions are now commonly in use, they nonetheless possess certain drawbacks. In general, currently available acrylic compositions are only poorly resistant to wearing and grinding and may stain easily. Moreover, their mechanical workability is poor and they tend to melt and smear when ground. Their resistance to heat and to solvents is often poor, and in some cases, they are hydrolytically unstable.

Accordingly, it is a principal object of this invention to provide compositions which are useful in the construction of artificial teeth and other dental appliances, which compositions lead to products having improved workability and superior physical and aesthetic characteristics.

DESCRIPTION OF THE PRIOR ART

It is to be understood that the term "bisphenol-A" is commonly utilized in the art to indicate the chemical compound 2,2-bis(4-hydroxyphenyl)propane. It is also to be understood that the term "bis-GMA" is commonly used to indicate the chemical compound 2,2-bis[4-(2-hydroxy-3-methacryloxypropoxy)phenyl]propane, otherwise referred to as "digycidyl methacrylate of bisphenol-A."

U.S. Pat. No. 3,084,436 to Laudry discloses soft dental materials manufactured from mixtures of methacrylate monomers. Monofunctional esters together with vinyl acetate or vinyl stearate are crosslinked with polyfunctional esters of acrylic or methacrylic acid. The resulting product is disclosed as being three dimensionally crosslinked.

The preparation of graft copolymers is disclosed by U.S. Pat. No. 3,087,875 to Graham et al. Alkyl methacrylate and analogous polymers are dissolved in monomers such as alkyl acrylates, alkyl thioacrylates, and N-vinyl lactams. The monomers are subsequently grafted to the pre-formed polymers via photochemical initiation.

U.S. Pat. No. 3,427,274 issued to Cornell describes hardenable materials formed from a mixture of methyl methacrylate homopolymer and styrene-butadiene copolymer latex coated with methyl methacrylate polymer which may be incorporated in a methacrylate-crosslinking agent composition to form hardenable compositions.

A dental restorative material is disclosed in U.S. Pat. No. 3,452,437 to Chang as being formed from the "diglycidyl methacrylate of bisphenol-A" (bis-GMA) to which a quantity of of methyl methacrylate may be added. Inorganic fillers, such as glass fiber or glass beads, may be included to modify the resultant matrix.

U.S. Pat. No. 3,468,977 to Bruckmann et al teaches the formulation of dental compositions from a mixture of a polymer and a monomer. The pre-formed uncrosslinked polymer beads are allowed to swell with monomer which may contain a crosslinking agent. Acrylic materials may be used for both the monomer and the polymer.

Petner, in U.S. Pat. No. 3,470,615, teaches the formulation of a material suitable for use in the construction of dental appliances. A mixture of an uncrosslinked homopolymer and crosslinked copolymer is dissolved in a liquid polyglycol dimethacrylate to form a suspension which may be brushed on a substratum and subsequently hardened by heat to build up layers of polymeric material. A similar teaching may be found in U.S. Pat. No. 3,471,596, also to Petner et al. A thick liquid is provided which is useful in the building up of dental crowns and the like. The difunctional monomer may contain various thickening agents including poly(methyl methacrylate). In some embodiments, the poly(methyl methacrylate) may be supplemented with additional polymer which may be partially crosslinked with allyl methacrylate.

U.S. Pat. No. 3,539,533 to Lee provides a filling material comprising a monomer solution filled with inorganic particulate filler. The monomer solution may be a mixture of methacrylate monomers containing bisphenol-A dimethacrylate.

Polyfunctional methacrylate monomers, including "bisphenol-A glycidyl dimethacrylate"(bis-GMA), may be polymerized together with an inorganic filler to yield dental compositions, as taught by U.S. Pat. No. 3,597,389 to Taylor.

U.S. Pat. No. 3,629,187 to Waller discloses the use of the isocyanate or diisocyanate adducts of bisphenol-A type compounds. These adducts are employed together with various inorganic fillers and liquid monomers to form liquid or paste compositions which are polymerizable either thermally or photochemically.

U.S. Pat. No. 3,647,498 to Dougherty discloses dental compositions which are composed of liquid-solid mixtures. The solid phase is an acrylate or methacrylate polymer in bead form, which polymer is not crosslinked. The liquid is a blend of polyglycol di-methacrylates and bisphenol-A dimethacrylate. Various modifications of bisphenol-A are disclosed as being especially useful.

In U.S. Pat. No. 3,649,608 to Logemann, dental compositions are taught which comprise solid bead polymers or copolymers of methacrylate type materials. These uncrosslinked materials are swollen in a liquid acrylate type monomer to yield useful products.

U.S. Pat. No. 3,751,399 to Lee discloses improved compositions for dental use comprising aromatic and alicyclic polyacrylates which are mixed together with other polyacrylate compounds especially those containing bisphenol-A structures. Inorganic fillers are specifically disclosed as being useful additives; pre-formed organic polymers are not used as fillers.

In U.S. Pat. No. 3,833,404 to Sperling, elastomers, especially acrylates, urethanes, butadienes, natural rubbers, and polyvinyl alcohol, are formulated which possess interpenetrating polymeric network type structures. These materials are disclosed as being "hard", but are used as vibration and sound damping insulators.

U.S. Pat. No. 3,961,379 to Highgate discloses an article manufactured from a crosslinked polymer which is swollen with a monomer containing a crosslinking agent. Thus, a replica of the finished article is swollen with the monomer solution which is then polymerized in situ. A finished, hard product is recovered. The material is not comprised of fungible materials, but rather is a unitary object entire and indivisible.

None of the foregoing patents discloses or suggests the novel hardenable compositions of the present invention.

SUMMARY OF THE INVENTION

In general, the novel compositions of this invention are useful for the formation, construction, and repair of dental appliances, artificial teeth, oral prosthetics, and similar articles. In addition, these compositions may be utilized for the filling of teeth, and for the surface coating thereof either to effect adhesion with oral prostheses, or to protect natural teeth from erosion, damage or decay.

In accordance with a preferred form of the present invention, hardenable dental compositions are provided which may easily and conveniently be molded by known techniques into prosthetic dental appliances possessing chemical and physical properties which are significantly improved over those of conventional prior art acrylic dental appliances. Notably, dental appliances such as, for example, prosthetic teeth produced from precursor blend compositions prepared in accordance with the invention are characterized by a grind resistance which is up to six times greater than the grind resistance of conventional plastic teeth commercially marketed at this time. Moreover, while conventional acrylic plastic teeth, upon grinding, tend to melt and curl yielding a soft plastic debris, teeth produced in accordance with the present invention yield fine, gritty debris upon grinding in generally the same fashion as do porcelain teeth.

Further, prosthetic teeth produced from the precursor blend compositions of the invention are characterized by a chemical resistance which far exceeds that of conventional acrylic plastic teeth and which approaches the chemical resistance of porcelain teeth. The solvent resistance of prosthetic teeth of the invention far surpasses that of commercially available acrylic teeth, as shown, for example, by the fact that prosthetic teeth produced from the precursor blends of the invention remain intact after three weeks of immersion in methyl methacrylate monomer, whereas conventional acrylic plastic teeth are structurally degraded by methyl methacrylate, usually in 24 hours or less.

Although possessing a superior chemical resistance, prosthetic teeth produced in accordance with the present invention have unexpectedly been found to establish an excellent chemical bond with commercial denture base systems using standard processing methods. Thus, teeth produced in accordance with the invention are superior to porcelain teeth in that they bond well to denture base, eliminating seepage between the tooth and denture base, thus avoiding foul odors and marginal staining.

In comparison to porcelain teeth, the prosthetic teeth produced in accordance with the invention are characterized as fracture resistant during denture processing and impact resistant should the denture be accidentally dropped into a porcelain sink or to the floor. The teeth described herein also give no clicking sound when occluded against each other in dentures as do porcelain teeth. In comparison with conventional acrylic teeth, the prosthetic teeth produced in accordance with the invention are characterized by outstanding monomer and solvent resistance; outstanding thermal stability, improved hardness, density, and stain resistance; and excellent hydrolytic stability. Some precursor blend compositions of the invention also provide teeth which are inherently opalescent. This characteristic enhances the appearance of the teeth, making the teeth more "natural" in appearance than conventional acrylic plastic teeth. Finally, teeth produced from the hardenable compositions of the invention exhibit excellent gloss when molded. During denture fabrication the gloss of these teeth is maintained better than that of conventional plastic teeth, due to superior chemical resistance.

The prosthetic teeth thus formed may be further characterized as having a heterogeneous microstructure. Such microstructure, which is believed to be functionally related to the superior physical characteristics of the articles formed in accordance with the practice of the invention, may be ascertained after proper preparation of a specimen of the articles through a suitable means of magnification.

Briefly stated, the hardenable dental compositions of the invention comprise a blend of components which, when combined in certain proportions and permitted to age or mature as hereinafter more fully described, produce a precursor blend that is moldable into prosthetic teeth and other dental devices. The precursor blend is formed in accordance with the invention by combining a crosslinked polymer with a monomer, a crosslinking agent for said monomer, and an optional uncrosslinked polymer and/or an initiator and by allowing said combination to age or mature. The crosslinked polymer is in the form of discrete particles having average diameters ranging from about 0.001 micron to about 500 microns. Preferably, at least 50% by weight of said particles have diameters less than about 150 microns, and more preferably, less than 100 microns. If desired, a mixture of two or more different crosslinked polymers may be used. A characteristic of the crosslinked polymer is that it will be insoluble in, but will be swollen by the liquid components used in the preparation of the precursor blend. Uncrosslinked polymer, if used, may be characterized as being capable of dissolving in or being dispersed by the liquid components of the blend. The liquid polymerizable monomer component of the compositions of the invention is a monomer having the capacity to dissolve or disperse such uncrosslinked polymer, dissolve or become miscible with the crosslinking agent, and swell the particles of crosslinked polymer used in the practice of the invention. If desired, a mixture of two or more such liquid polymerizable monomers may be used.

It has been discovered that the relative proportions of the components of the precursor blend produced in accordance with the invention are critical to the attainment of the desired properties in the final hardened or cured product produced therefrom, notably the grind resistance, wear resistance, bond strength, impact resistance, resistance to monomer and other solvents, stain resistance, thermal stability, and hydrolytic stability. Thus, it has been discovered that blends of from about 10 to about 70 weight percent of the crosslinked polymer, from about 0 to about 50 weight percent of the uncrosslinked polymer, from about 2 to about 30 weight percent of polymerizable monomer, and from about 20 to about 70 weight percent of crosslinking agent for said monomer, together with minor amounts of initiator and in some cases activator for the initiator, provide blends which are particularly useful in the production of prosthetic teeth and denture bases characterized by properties far superior to those of conventional acrylic systems now used in the art. Prosthetic teeth possessing outstanding grind resistance, wear resistance, resistance to monomer and other solvents, stain resistance, thermal stability, and hydrolytic stability may be produced in accordance with the present invention from precursor blends including from 40 to 60 percent by weight of crosslinked polymer, from 13 to 34 weight percent of uncrosslinked polymer, from 2 to 5 percent by weight of polymerizable monomer, from 40 to 60 percent by weight of crosslinking agent, and up to about 2 percent by weight of initiator.

In general, the crosslinked polymers which are useful in the practice of the invention are formed from monomers or blends of monomers together with crosslinking agents in proper proportion. The monomers suitable for use in the production of the crosslinked polymers useful in the practice of the invention, will generally comprise any of a wide variety of monomers such as, for example, acrylic and lower alkyl acrylic acid esters, N-vinyl lactams, acrylamides, acrylonitriles, styrenes, alkenes, and urethanes. Similarly, mixtures of two or more monomers may be employed to provide these crosslinked polymers.

Preferred monomeric species useful in the preparation of the crosslinked polymers of the invention include acrylic and lower alkyl acrylic acid esters which generally conform to the structure:

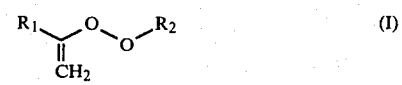

where $R_1$ is hydrogen or an alkyl group including from 1 to about 6 carbon atoms, and where $R_2$ is either (a) an alkyl or cycloalkyl group including from 1 to about 20, and preferably from 1 to about 6 carbon atoms; (b) phenyl; and (c) alkyl substituted phenyl in which the alkyl groups include from 1 to about 6 carbon atoms. Various substituents may be present on either or both of the groups $R_1$ and $R_2$. Thus, hydroxyl, amino, thiol and halogen (e.g., fluorine, chlorine, etc.) functionalities may be present, with the latter being preferred. Fluorine is an especially suitable and useful substituent.

Especially preferred examples of monomers useful in the production of the crosslinked polymers used in the practice of the invention include methyl-, ethyl-, isopropyl-, tert-butyloctyl-, dodecyl-, cyclohexyl-, chloromethyl-, tetrachloroethyl-, perfluorooctyl-, hydroxyethyl-, hydroxypropyl-, hydroxybutyl-, 3-hydroxyphenyl-, 4-hydroxyphenyl-, aminoethyl-, aminophenyl-, and thiophenyl-, acrylate, methacrylate, ethacrylate, propacrylate, butacrylate and chloromethacrylate, as well as the homologous mono-acrylic acid esters of bisphenol-A, dihydroxydiphenyl sulfone, dihydroxydiphenyl ether, dihydroxybiphenyl, dihydroxydiphenyl sulfoxide, and 2,2 bis(4-hydroxy-2,3,5,6-tetrafluorophenyl)propane. Other suitable species will be apparent to those skilled in the art. If desired, mixtures of two or more different monomers may be used to provide the crosslinked polymers useful in the practice of the invention.

The crosslinking agents which are useful in the production of the crosslinked polymer component of the invention comprise a wide variety of di- or polyfunctional moieties which are capable of crosslinking monomer species. In general, the reactive functionalities which serve as active sites for such crosslinking are ethylenic functions, but other reactive and effective crosslinking functions are similarly useful as will be hereinafter described. The use of crosslinking agents in the formulation of polymers is well known to those skilled in the art, who similarly recognize that it is necessary for such agents to have at least two reactive functionalities.

Suitable crosslinking agents may be selected from numerous families of polyfunctional monomers such as acrylic and lower alkyl acrylic acid diesters, acrylic and lower alkyl acrylic acid esters formed from alcohols, which alcohols have a second reactive function, urethane diacrylates and dimethacrylates, polyvinylic compounds, divinyl aromatic compounds and others, as will be apparent to those skilled in the art.

Preferably, the crosslinking agents comprise esters of unsaturated acids, e.g., acrylic, methacrylic, ethacrylic, propacrylic, butacrylic, etc., maleic, fumaric, citraconic, mesaconic, itaconic, malonic, or aconitic, etc., acids. Other unsaturated acids will be readily apparent to those skilled in the art. These acids are preferably reacted with either unsaturated or polyhydroxylic alcohols to form esters which are effective polyfunctional crosslinking agents useful in the formulation of the crosslinked polymers of the invention. In general, these alcohols have one or more hydroxylic functionalities and have from 2 to about 30 carbon atoms. Thus, useful alcohols include allyl, methallyl, crotyl, vinyl, butenyl, isobutenyl and similar unsaturated alcohols as well as polyols such as ethylene glycol, propylene glycol, butylene glycol, diethylene glycol, triethylene glycol, tetraethylene glycol, pentaethylene glycol, glycerol, 1,3,3-trimethylolpropane, pentaerythritol, dihydroxyphenol, and alkylidene bisphenols such as bisphenol-A, 1,1-bis(4-hydroxyphenyl)methane, 4,4'-dihydroxybiphenyl, 4,4'-dihydroxydiphenyl sulfone, dihydroxydiphenyl ether, dihydroxydiphenyl sulfoxide, resorcinol, hydroquinone, etc.

Crosslinking agents preferred for the practice of the invention include the esters of a mono- or dibasic unsaturated acid with an unsaturated monohydroxylic alcohol such as allyl acrylate, allyl methacrylate, vinyl acrylate (methacrylate and $C_1$ to $C_{20}$ homologs), dimethallyl fumarate, N-allyl acrylamide, crotyl acrylate, allyl crotonate, allyl cinnamate, diallyl maleate, etc. Other preferred species are the di-, tri-, and higher esters of polyhydroxylic alcohols such as ethylene "glycol" diacrylate (dimethacrylate and $C_2$-$C_{40}$ homologs), trimethylolpropane trimethacrylate, and the diacrylate and dimethacrylate esters of bisphenol-A as well, as acrylate and alkyl acrylate esters which correspond to the general formula

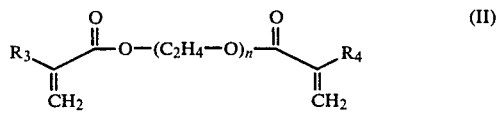

(II)

where $R_3$ and $R_4$ may be the same or different and are hydrogen or alkyl groups containing from 1 to about 6 carbon atoms and n is a whole number from 1 to about 10. Alternatively, the crosslinking agent may conform to the formula

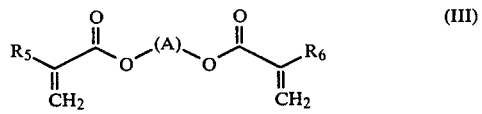

(III)

where $R_5$ and $R_6$ may be the same or different and are hydrogen or alkyl groups containing from 1 to about 6 carbon atoms and A is an aromatic moiety selected from the group consisting of (a) biphenyl, diphenyl alkylidene having from 1 to about 6 carbon atoms in the alkylidene portion thereof, diphenyl sulfone, diphenyl sulfoxide, diphenyl ether, and diphenyl sulfide; (b) the diglycidyl derivatives of group (a); and (c) the diurethane derivatives of either group (a) or group (b). In addition, the crosslinking agent may be a glycidyl acrylate or allyl acrylate, divinyl (trivinyl or higher homologs) benzene, substituted divinyl benzenes, and analogous compounds. Furthermore, mixtures of two or more crosslinking agents are useful in the practice of the invention.

Compounds such as bis-GMA and the urethane diacrylic formed by reacting hydroxyethyl acrylate hydroxypropyl acrylate and their methacrylic homologs with 2,2,4-trimethylhexyl-1,6-diisocyanate are especially useful, as are diallyl maleate, ethylene "glycol" dimethacrylate, trimethylolpropane trimethacrylate and the dimethacrylate ester of bisphenol-A.

The crosslinked polymers are produced by polymerizing a mixture of the monomer or monomers and crosslinking agent or agents described above. The amount of crosslinking agent employed in the production of the crosslinked polymers used in the practice of the invention is a critical factor. It has been found that the capacity of particles of polymers so produced to swell with or to imbibe the liquid components forming the precursor blend of the invention, is directly related to the amount of crosslinking agent used in the production of such crosslinked polymers.

The physiochemical properties of the crosslinked polymers useful in the practice of the invention determine the relative proportions of monomer and crosslinking agent used to formulate said suitable crosslinked polymers. Such crosslinked polymers must be sufficiently well crosslinked as to maintain substantially their structural identity when exposed to the liquid components of the precursor blend of the invention. At the same time, they must not be so thoroughly crosslinked as to be incapable of swelling with or imbibing such liquid components. Thus, it is convenient to describe the proportion of crosslinking agent by what it does rather than by what it is. In view of the fact that the crosslinked polymers are utilized in finely particulate form, as will be more fully explained, it is convenient to define the minimum amount of crosslinking agent used therein as being that amount which is sufficient to cause the particulate crosslinked polymer not to lose its particulate discreteness upon exposure to the liquid components of the invention. Similarly, the maximum amount of crosslinking agent used therein is that amount beyond which the resulting crosslinked polymer particles are unable to swell with or further imbibe a significant portion of liquid components upon exposure thereto. In this regard, a quantity of crosslinked polymer particles would be said to swell with or imbibe a significant portion of liquid components if it swelled with or has imbibed at least 10% of its own weight of such liquid. Preferably, an amount of crosslinking agent is used to provide a crosslinked polymer having the capacity to imbibe from about 10 to about 500 percent of its own weight of liquid components.

It will be clear to those skilled in the art that the minimum and maximum values for the proportions of crosslinking agents suitable for inclusion in the crosslinked polymers of this invention will vary depending upon the chemical identity of the component monomers and crosslinking agents. In general, however, the crosslinking agents may comprise from as low as about 0.01% to as high as about 30% and preferably from about 0.2% to about 18% by weight of the resulting crosslinked polymer. For any monomer-crosslinking agent system, it is well within the routine knowledge of those skilled in the art to ascertain the optimum proportion of crosslinking agent in view of the requirements set forth above.

The production of the crosslinked polymers useful in the practice of this invention from monomers and crosslinking agents may be performed by any of the many processes known to those skilled in the art. Thus, the polymers may be formed by heating a mixture of the components to a temperature sufficient to cause polymerization, either with or without the addition of initiators. For this purpose, peroxy type initiators such as benzoyl peroxide, dicumyl peroxide and other materials familiar to those skilled in the art may be employed, and the use of activators may be advantageous in some formulations. Alternatively, the crosslinked polymers of the invention may be formed from the constituents by photochemical or radiant initiation utilizing light or high energy radiation. For photochemical initiation, photochemical sensitizers or energy transfer compounds may be employed to enhance the overall polymerization efficiency in manners well known to those skilled in the art.

The polymerization of the crosslinked, polymers may be accomplished in a wide variety of ways, all of which are known to those skilled in the art. Thus, they may be formed by suspension polymerization as taught in U.S. Pat. No. 2,673,194 to Grim, emulsion polymerization, block polymerization or any other useful and convenient process. Since, as will be more fully described herein, it is desirable to have the crosslinked polymer available in the form of finely particulated granules or beads, suspension polymerization is especially convenient. Blocks of bulk-formed polymer may be crushed to yield a useful product, however. The size of the particles of crosslinked polymer is of significance to the invention. As indicated, it is desirable that the crosslinked polymer be in the form of small, discrete particles or beads. The average particle size should be from about 0.001 micron to about 500 microns. It is preferred that at least 50% by weight of the particles have diameters below 150 microns and more preferably below 100 microns.

In addition to the crosslinked polymers described above, the polymer component of the precursor blend may comprise an uncrosslinked polymer. Such uncrosslinked polymer is formed from any of the monofunctional monomer species which have been disclosed above as being useful for the preparation of the crosslinked polymers used in the practice of the invention. Thus, monomer species conforming to Formula I above, the acrylic and $C_1$ to $C_6$ lower alkyl acrylic esters of aliphatic alcohols or phenols having from 1 to about 20 carbon atoms, or mixtures thereof, are suitable as is vinylidene fluoride. Polymeric methyl methacrylate and methyl acrylate are preferred. While moieties conforming to Formula I above are most preferred, each and any of the other materials disclosed as being monofunctional monomers suitable for inclusion in the crosslinked polymer are also suitable materials for use in formulation of the uncrosslinked polymers. Mixtures of monomers are also quite useful. The uncrosslinked polymers may be formed from the monomers through any of the polymerization procedures known to those skilled in the art. Thus, thermal or photochemical polymerization, either with or without initiators, sensitizers, activators, or chain transfer agents, may be employed. Similarly, either bulk or suspension polymerization may be utilized. Preferably, the uncrosslinked polymers should be characterized as having average molecular weights of from about 100,000 to about 2,000,000 g/mole, and especially of from about 500,000 to about 900,000 g/mole. While the polymers are used in particulate form, they differ from the crosslinked polymers in that, unlike the crosslinked polymers, the uncrosslinked polymers do not have a critical particle size distribution. Thus, polymer particles or beads of any conveniently small size, such as about 500 microns, may be utilized. Smaller sizes are preferred since they imbibe monomers and will dissolve therein more readily, but larger sizes may be used as well.

The uncrosslinked polymers used in the practice of the present invention are quite distinct from the crosslinked polymers. The crosslinked polymers have been defined as being capable of swelling with or imbibing the liquid componentsof the precursor blend of the invention, and as being of a physical and physiochemical structure so as not to lose their discrete particulate identity upon such swelling. This physical definition has, similarly, been related to the proportion of crosslinking agent included therein. By comparison, the particles of uncrosslinked polymer do not retain their particulate discreteness when exposed to the liquid components, but are dissolved therein if sufficient time and liquid components are provided.

The polymerizable monomers suitable for use in the formulation of the precursor blend of the invention may comprise any of a wide variety of monomers. Thus, acrylic and lower alkyl acrylic acid esters, N-vinyl lactams, acrylamides, acrylonitriles, styrenes, alkenes, urethane acrylate or methacrylate, and other monomeric species may be employed in the practice of the invention.

Preferred monomeric species are acrylic and lower alkyl acrylic acid esters which may be seen generally to conform to Formula I, above. Especially preferred examples of polymerizable monomers useful in the practice of the invention include methyl-, ethyl-, isopropyl-, t-butyl-, octyl-, dodecyl-, cyclohexyl-, chloromethyl-, tetrachloroethyl-, perfluorooctyl-, hydroxyethyl-, hydroxypropyl-, hydroxybutyl-, 3-hydroxyphenyl-, 4-hydroxyphenyl-, aminoethyl-, aminophenyl-, and thiophenyl-, acrylate, methacrylate, ethacrylate, propacrylate, butacrylate and chloromethacrylate, as well as the homologous mono-acrylic acid esters of bisphenol-A, dihydroxydiphenyl sulfone, dihydroxydiphenyl ether, dihydroxybiphenyl, dihydroxydiphenyl sulfoxide, and 2,2-bis(4-hydroxy-2,3,5,6-tetrafluorophenyl)-propane. Other suitable species will be apparent to those skilled in the art who will further recognize that mixtures of two or more different polymerizable monomers may be used.

As noted above, the polymerizable monomer components of the precursor blends of the invention are generally liquid at room temperature and have the capacity to dissolve or disperse the uncrosslinked polymers and to swell or be imbibed by the crosslinked polymers which further comprise the precursor blend. Furthermore, the polymerizable monomers are capable of being crosslinked by the crosslinking agents as will be described below.

The crosslinking agents for the polymerizable monomers useful in the practice of the invention comprise a wide variety of di- or polyfunctional moieties which are capable of crosslinking monomeric species. In general, the reactive functionalities which serve as active sites for this crosslinking are ethylenic functions, but other reactive crosslinking functions are similarly useful. The use of crosslinking agents in the formulation and elaboration of polymers is well known to those skilled in the art, who will appreciate that it is necessary for such agents to have at least two reactive functionalities. Suitable crosslinking agents may be selected from numerous families of polyfunctional monomers such as acrylic and lower alkyl acrylic acid diesters, acrylic and lower alkyl acrylic acid esters formed from alcohols which alcohols have a second reactive function, urethane diacrylates and dimethacrylates, polyvinylic compounds, divinyl aromatic compounds and others as will be apparent to those skilled in the art.

Preferably, the crosslinking agents for the polymerizable monomers comprise esters of unsaturated acids, e.g., acrylic, methacrylic, ethacrylic, propacrylic, butacrylic, etc., maleic, fumaric, citraconic, mesaconic, itaconic, malonic, or aconitic, etc., acids. Other unsaturated acids will be readily apparent to those skilled in the art. These acids are preferably reacted with either unsaturated or polyhydroxylic alcohols to form esters which are effective polyfunctional crosslinking agents for the monomeric species useful in the practice of the invention. Thus, useful alcohols include allyl, methallyl, crotyl, vinyl, butenyl, isobutenyl and similar unsaturated alcohols as well as polyols such as ethylene glycol, propylene glycol, butylene glycol, diethylene glycol, triethylene glycol, tetraethylene glycol, pentaethylene glycol, glycerol, trimethylolpropane, pentaerythritol, dihydroxyphenol, alkylidene bisphenols such as bisphenol-A; 1,1-bis(4-hydroxyphenyl)methane; 4,4'-dihydroxybiphenyl; 4,4'-dihydroxydiphenyl sulfone; dihydroxydiphenyl ether; dihydroxydiphenyl sulfoxide; resorcinol; hydroquinone; etc.

The preferred crosslinking agents used in the practice of the invention include the esters of a monomeric dibasic unsaturated acid with an unsaturated monohydroxylic alcohol such as allyl acrylate, allyl methacrylate, vinyl acrylate (methacrylate and homologs), dimethallyl fumarate, N-allyl acrylamide, crotyl acrylate, allyl crotonate, allyl cinnamate, diallyl maleate, etc. Other preferred species are the di-, tri-, and higher esters of polyhydroxylic alcohols such as ethylene "glycol" diacrylate (dimethacrylate and $C_2$-$C_6$ homologs), trimethylolpropane trimethacrylate, and the dimethacrylate ester of bisphenol-A as well as other acrylate and alkyl acrylate esters corresponding to Formula II, above. Alternatively, the crosslinking agent may conform to Formula III, above. In addition, the crosslinking agent for the polymerizable monomers may be a glycidyl acrylate or allyl acrylate, divinyl (trivinyl or higher homologs) benzene, substituted divinyl benzenes, or analogous compounds. Furthermore, mixtures of crosslinking agents are useful in the practice of the invention.

Compounds such as bis-GMA and the urethane dimethacrylate formed from the reaction of hydroxyethyl acrylate, hydroxypropyl acrylate and their methacrylate homologs with 2,2,4-trimethylhexyl-1,6-diisocyanate (hereinafter referred to as "urethane dimethacrylate" or "diacrylate") are especially useful, as are ethylene "glycol" dimethacrylate, trimethylolpropane trimethacrylate and the dimethacrylate ester of bisphenol-A. The corresponding acrylates are similarly useful as is diallyl maleate.

In addition to the components described above, (i.e., crosslinked polymer, uncrosslinked polymer, polymerizable monomer and a crosslinking agent for the polymerizable monomer) the precursor blend further may contain additional, optional, ingredients. These may comprise initiators, activators, pigments, fillers, radiopaquing agents, adhesion modifiers and other materials as will occur to those skilled in the art. This, it is useful to include free radical or photochemical initiators in the precursor blend composition of the invention to cause modification of the hardening kinetics thereof. In this regard, peroxy type initiators such as dicumyl or benzoyl peroxide are useful. Similarly, pigments and fillers may be added to modify the appearance, density, and physical characteristics of the resultant dental appliances. Inorganic materials, especially silica and titania, are useful fillers and pigments while a wide variety of other useful pigments and fillers will be apparent to those skilled in the art. The fillers and radiopaquing agents may constitute a major part by weight of the compositions of the invention. According to a preferred embodiment, the precursor blend of this invention may comprise admixtures of organic resin components and particulate, inorganic filler in weight ratios of from about 1:2 to about 2:1.

The precursor blends of the invention are formulated by a mixing together of the constituent species in proper proportion, followed by aging or maturing. Several techniques are available for this and others will be apparent to those skilled in the art. Thus, it is possible to combine crosslinked polymer, uncrosslinked polymer, polymerizable monomer and a crosslinking agent for said monomer in proper proportions including therewith, for example, a peroxide initiator and a pigment. This combination is then thoroughly mixed and aged to result in a precursor blend which has a uniform appearance. This blend may have the consistency of dough or may be more or less mobile depending upon the desired use therefor. Particulate inorganic fillers or other modificants may be preferably added at this stage in the formulation of the compositions if desired. The compositions thus formed may be alternatively molded, extruded, brushed, formed, worked or otherwise shaped in any conventional manner and caused to polymerize or cure to result in hard dental appliances having superior properties. The application of heat or radiant energy is usually required, for this polymerization or curing.

It is especially useful to mold the compositions of this invention into artificial teeth for inclusion in prosthetic devices. It is to be understood, however, that the precursor blends are suitable for a very wide range of dental uses, including fillings, teeth, bridges, crowns, veneers, facings, pit and fissure sealants, denture base and denture reline materials, orthodontic splint materials, and adhesives for orthodontic appliances. The materials of the invention may also be utilized for prosthetic replacement or repair of various hard body structures such as bone and may be utilized for reconstructive purposes during surgery, especially oral surgery. They are also useful for various non-dental uses as, for example, in plastic construction materials.

The nature of the chemical and physical relationships among the components of the precursor blends of the invention is important to the practice of the invention. Chief among these relationships is the necessity that the crosslinked polymer particles be capable of swelling with or imbibing the liquid components of the invention. Of similar importance is the requirement that the uncrosslinked polymers, when included, be capable of dissolving in the liquid components. In accordance with the invention, the precursor blend formed by any of the useful techniques described above is aged for a period of time sufficient to insure that the crosslinked polymer has become substantially fully swollen with, interpenetrated by or has substantially imbibed the monomer-crosslinking agent mixture and that the uncrosslinked polymer, if used, has substantially dissolved therein. Thus, as used herein, "aged" or "aging" refer to the maintenance of the components of the precursor blend in association with one another in the blend for a period of time sufficient to substantially fully swell the crosslinked polymer particles with the mixture of polymerizable monomer and crosslinking agent dissolved therein. Frequently, the aging process is manifested by a change in the consistency of the mixture as equilibrium is approached. The time necessary to approach such equilibrium will vary depending upon the blending techniques, the relative proportions of materials, the particle sizes and molecular weights of the polymers and the temperature extant in the mixtures. In general, aging time of from one to seven days has been found to be adequate to approach the desired equilibrium. It is to be understood that it lies well within the abilities of those skilled in the art to ascertain the optimum aging time for a formulation in view of the foregoing considerations.

A further technique especially useful for the formulation of the precursor blends of the invention, denominated as the preswell method, causes the crosslinked polymer particles to swell with or imbibe a mixture of polymerizable monomer and crosslinking agent for said monomer at a time remote from and preceding the final mixing of the ultimate precursor blend. In accordance with this preferred technique, the crosslinked polymer particles are blended with a mixture of polymerizable monomer and crosslinking agent (dissolved in said monomer). The blend is then aged for a period of time sufficient to permit the crosslinked polymer particles to be substantially fully swollen with, or interpenetrated by the monomer-crosslinking agent mixture. In general, an amount of monomer is selected which will be completely imbibed by the crosslinked polymer particles with which the monomer is combined. This "preswollen" crosslinked polymer-monomer combination may subsequently be mixed with uncrosslinked polymer and further quantities of polymerizable monomer and crosslinking agent to form the precursor blend. This technique affords savings in time and results in greater convenience in the formulation of the precursor blends of the invention due to the fact that aging has taken place in advance of final mixing. Precursor blends thus formed may be alternatively molded, brushed, extruded, formed, worked or otherwise shaped in manners similar to those useful with batch mixing techniques to form similarly useful articles. Other techniques are presented in the examples which follow, and still others will be apparent to those skilled in the art.

Upon polymerization of the precursor blends, a three dimensional structure is believed to be formed which may be denominated as an interpenetrating polymeric network or IPN. The IPN structure which is thought thus to form is believed to be a major contributing factor to the serendipitous combination of superior chemical and physiochemical properties which is exhibited by the articles constructed according to the practice of the invention. Interpenetrating polymeric networks are related to, but distinct from, traditional graft polymers. In general, when a second polymer is synthesized in the intimate presence of a first polymer, the resultant material has been known as a graft polymer regardless of the actual extent of chemical grafting of one polymer to the other. IPN's are thought to be formed, however, when the first polymer is substantially crosslinked into a three dimensional network prior to the formation of the second polymer, and when that second polymer is caused to form in such a fashion that it too is substantially crosslinked into a three dimensional network. Such network may also "suspend" inclusions of inorganic origin such as, for example, pigments and fillers.

Thus, an IPN may be viewed as being composed of two or more crosslinked, and hence three dimensionally arrayed, polymeric networks which co-exist in the same volume of space, but which do not necessarily have any covalent bonds in common. While the two networks may, indeed, be independent in the sense that they need posess no covalent linkages between them; they are physically trapped one "within" the other and cannot disassociate by any physical manipulation without the rupture of covalent bonds.

Central to an understanding of interpenetrating polymeric networks is the recognition that an IPN is not a substance per se, but is, rather, a term descriptive of a structure. For discussions of the nature of IPN's in general, see the recent papers by L. H. Sperling et al, *Macromolecules*, vol. 9, No. 4 (1976)pages 671–680, *Macromolecules*, vol. 9, No. 5 (1976)pages 743–749; *J Polymer Science*, vol. 12, page 141 (1977); and *J Polymer Science*, vol. 16, page 583 (1978); and articles cited therein. Also, see Klepner et al, *J Elastoplast*, vol. 5, page 196 (Oct. 1973).

While it appears to be desirable that the crosslinking of both polymers be substantial, various degrees of crosslinking are possible in both the preformed polymer and the polymer formed in situ. In addition, it should be recognized that an IPN may be formed even when the initial and second polymers are formed from the same materials. For example, two independent networks of a polymethacrylate, suitably crosslinked, may interpenetrate each other to form an IPN. Similarly, an IPN need not be limited only to two networks, as mixtures of two or more polymers may be used as the initial polymer, and mixtures of two or more monomers may be employed to form a second polymeric network. Mixtures of two or more crosslinking agents may also be used in either network formation.

It is thought that in the present invention, interpenetrating polymeric networks may be formed. Thus, when particulate crosslinked polymer is allowed to swell with or imbibe monomer mixed with crosslinking agent, and when the imbibed mixture of monomer and crosslinking agent is subsequently caused to polymerize, an interpenetrating polymeric network may be seen to be formed within the confines of the particulate crosslinked polymer. It is believed that it is this interpenetrating polymeric network structure, which is localized in the particulate masses formed subsequent to the swelling of particulate crosslinked polymer and the polymerization of the precursor blend, that lends the superior chemical and physiochemical properties to the articles formed according to this invention. It is believed that the aging process employed in the preparation of the precursor blends of the invention is required to accomplish substantially full swelling with interpenetration by or substantially complete inhibition of monomer-crosslinking agent by the crosslinked polymer particles, and to approach an equilibrium thereof. It is to be understood, however, that the foregoing discussion of interpenetrating polymeric networks and their application to the present invention is not to be construed as a limiting factor thereof, but, rather, is to be interpreted as a mechanism which is proposed as being applicable in the present case.

As has been indicated, the compositions of the invention exhibit superior chemical and physiochemical properties. Accordingly, the articles made from the compositions of the invention exhibit superior grind resistance, monomer resistance, and bonding strength to denture bases. In addition, such articles display a unique microstructure.

Resistance to grinding may be demonstrated either qualitatively or quantitatively. Qualitatively, present plastic teeth tend to melt and curl when ground upon, whereas dental compositions disclosed herein exhibit a fine, dusty debris like that of porcelain teeth when ground upon in like manner using various speeds, torques, and hand pressures as follows:

1. Low Speed/High Torque Dental Lathe—Dedeco "Fast Tooth Grinding" wheel or Cratex 318-C wheel driven at 1740 or 3450 r.p.m. by a Red Wing dental lathe.
2. Low Speed/High Torque Dental Handpiece—An alundum or silicon carbide mounted point driven at 1400 r.p.m. by a belt-drive Foredom dental handpiece.
3. Moderate Speed/High Torque Dental Handpiece—An alundum or silicon carbide mounted point driven at 20,000 to 30,000 r.p.m. by a Dentsply Dentatus TM dental handpiece.
4. High Speed/Low Torque Dental Handpiece—An alundum or silicon carbide mounted point driven at 250,000 to 350,000 r.p.m. by a Dentsply Silencer TM dental handpiece.

Quantitative grind resistance is best measured through application of the test method detailed in the paper entitled *Quantitative Abrasive Grind Resistance Test* presented by F. Roemer, L. Tateosian and J. Glenn at the 55th meeting of the American Association for Dental Research, 1977, Las Vegas, Nev. Typical grind resistance values, depending on composition, are 90–140 g/sec. for present acrylic teeth; 450–550 g/sec. for the dental compositions disclosed herein; and 700/800 g/sec. for present porcelain teeth. Thus it is apparent that the present material is qualitatively and quantitatively superior to conventional plastic teeth in terms of grind resistance.

Porcelain teeth exhibit excellent methyl methacrylate (MMA) resistance; they do not bond chemically to conventional denture base materials, however. The dental compositions disclosed herein exhibit excellent MMA resistance relative to present acrylic teeth. Immersed in MMA monomer at 23° C., present acrylic teeth will blanch, swell to one-and-one-half normal size or larger, crack, partially dissolve, and/or lose their original integrity within the first 24 hours of monomer contact. Teeth formed according to this invention do not exhibit any significant attack distortion after immersion in 23° C. MMA monomer for one week. Teeth formed from the preferred compositions have exhibited negligible attack after immersion in 23° C. MMA for 27 days.

The American Dental Association specification number 15 specifies, "the strength of the bond between tooth and resin is tested in tension. The minimum bond strength is 30.9 MN/m$^2$ (4,480 psi; 315 Kg/cm$^2$), which is sufficient to prevent separation of the teeth from the resin denture base in use." This pertains to "acrylic denture base resin polymerized by the heat processing technique." The compositions of this invention meet or exceed this specification.

A unique, heterogeneous microstructure is exhibited by the compositions of this invention. One exemplary method for observing this microstructure is as follows:

1. The tooth, or molded article, is sectioned and one section potted in epoxy against a flat surface.
2. The sectioned surface of the potted specimen is polished to a smooth surface using nos. 320, 400 and 600 grit silicon carbide papers wet continuously with water.
3. A final polish is obtained using an aqueous slurry of 0.3 micron Al$_2$O$_3$ on a chammy.
4. The polished surface of the section is exposed for four minutes to the vapors of boiling concentrated nitric acid; the microstructure is oxidatively disclosed by this etching procedure and is best captured by photomicrography at 260×magnification.

The microstructure thus observed is heterogeneous and comprises what may best be described as particles suspended in a matrix. These particles are believed to be identifiable with the particulate crosslinked polymers of the precursor blend which have been swollen by and interpenetrated with the monomer and crosslinking agent. By comparison with conventional composite compositions containing only rigid inorganic fillers, the articles formed according to the present invention exhibit a microstructure in which the structure is much more closely packed. It is to be understood that this methodology, while of wide application in the examination of the microstructure of the novel compositions of the invention, is not exclusive. Other techniques involving greater or lesser magnification and other means of visualization are also useful in disclosing the structure.

The following examples describe certain representative embodiments of this invention and will serve further to illustrate the nature thereof. It is to be understood that the examples are merely illustrative, and do not in any way limit the scope of the invention as defined by the claims. All percentages are by weight.

PROSTHETIC TEETH

EXAMPLE 1

A precursor blend was prepared from the following composition:

| | |
|---|---|
| 47.83% | methyl methacrylate |
| 0.17% | benzoyl peroxide |
| 12.00% | 2,2-bis(4-methacryloxyphenyl)propane |
| 25.80% | poly(methyl methacrylate-co-ethylene dimethacrylate) (98.4:1.6) |
| 12.40% | poly(methyl methacrylate) |
| 1.80% | pigment |
| 100.00% | |

The crosslinked polymer was in the form of particles, 46% by weight of which were below 74 microns in size, the balance being below about 500 microns in size. The poly(methyl methacrylate) had an average molecular weight of 800,000 g/mole.

The benzoyl peroxide and 2,2-bis(4-methacryloxyphenyl)propane were dissolved in the methyl methacrylate at ambient temperature to form a monomer solution. The polymers and pigment were charged to a planetary dough mixer containing the monomer solution and the charge was stirred until visibly homogeneous. Prosthetic teeth were molded from the resultant precursor blend mixture after it was aged at ambient temperature for seven days. The resulting teeth grind with a dusty, fine debris, bond to denture base and are impact and wear resistant.

EXAMPLE 2

The method described in Example 1 was used to prepare a precursor blend from which prosthetic teeth were molded having the following composition:

| | |
|---|---|
| 27.83% | methyl methacrylate |
| .17% | benzoyl peroxide |
| 2.11% | 2,2,2-trifluoroethyl acrylate |
| 2.37% | ethylene 'glycol' dimethacrylate |
| 1.52% | urethane diacrylate |
| 43.30% | poly(methyl methacrylate-co-ethylene dimethacrylate) (98.8:1.2) |
| 21.65% | poly(methyl methacrylate) |
| 1.05% | pigment |
| 100.00% | |

A suitable gel-like consistency for molding prosthetic teeth was obtained after aging at ambient temperature for 24 hours.

EXAMPLE 3

The following composition yielded a precursor blend which could be molded into prosthetic teeth after processing according to the technique of Example 1:

| | |
|---|---|
| 47.83% | methyl methacrylate |
| 0.17% | benzoyl peroxide |
| 12.00% | bis-GMA |
| 25.80% | poly(methyl methacrylate-co-ethylene dimethacrylate) (70:30) |
| 12.40% | poly(methyl methacrylate) |
| 1.80% | pigment |
| 100.00% | |

EXAMPLE 4

A two-step "preswell" mixing method was used to prepare a precursor blend from which prosthetic teeth were molded, said blend having the following composition:

| Step 1 | |
|---|---|
| 42.40% | methyl methacrylate |
| 0.25% | benzoyl peroxide |
| 6.00% | urethane diacrylate |
| 1.50% | 2,2-bis(4-methacryloxyphenyl)propane |
| 49.85% | poly(methyl methacrylate-co-ethylene dimethacrylate) (90:10) |
| 100.00% | |

The crosslinked polymer was in the form of particles, 50% by weight of which were below 100 microns in size, the balance being below about 500 microns in size.

| Step 2 | |
|---|---|
| 28.14% | poly(methyl methacrylate) |
| 60.43% | methyl methacrylate |
| 0.36% | benzoyl peroxide |
| 10.20% | 2,2-bis(4-methacryloxyphenyl)propane |
| 0.87% | pigment |
| 100.00% | |

The poly(methyl methacrylate) had an average molecular weight of 850,000 g/mole.

The weight ratio of Step 1 to Step 2 material in this example is 1.14 to 1.00. Step 1 was achieved by preparing a solution of the monomers, crosslinkers and initiator and adding the crosslinked copolymer. This mixture was stirred for about two minutes to wet the polymer, capped against monomer loss, and held for one week at ambient temperature. The crosslinked copolymer completely absorbed the monomer solution during the one week "preswell" period. Although the copolymer was swollen by this process, the integrity of the individual copolymer particles was maintained. This "preswell" mixture was not gel-like, but had the consistency of a rubbery, spongy mass which was easily crumbled.

Step 2 was achieved by charging "preswell", obtained in Step 1, to a planetary dough mixer and mixing sufficiently so as to break the "preswell" mass down to a fine consistency. The poly(methyl methacrylate) and pigment were added to the mixer and mixing was continued until a homogeneous dispersion was obtained. The solution of monomer and initiator, cited in the Step 2 composition, was charged to the mixer; mixing continued until a homogeneous, gel consistency was obtained. The gel-like mix was transferred to a holding container and aged at ambient temperature until a suitable consistency for molding prosthetic teeth was obtained, approximately three days.

EXAMPLE 5

The two-step "preswell" method described in Example 4, was used to prepare a precursor blend from which prosthetic teeth were molded having the following composition:

| Step 1 | |
|---|---|
| 39.90% | methyl methacrylate |
| 0.24% | benzoyl peroxide |
| 9.98% | 2,2-bis(4-methacryloxyethoxyphenyl)propane |
| 49.88% | poly(methyl methacrylate-co-ethylene dimethacrylate) (98:2) |
| 100.00% | |

| Step 2 | |
|---|---|
| 36.37% | poly(methyl methacrylate) |
| 49.92% | methyl methacrylate |
| .32% | benzoyl peroxide |
| 12.19% | 2,2-bis(4-methacryloxyethoxyphenyl)propane |
| 1.20% | pigment |
| 100.00% | |

The weight ratio of Step 1 to Step 2 material in this example is 0.46 to 1.00. A suitable gel-like consistency for molding prosthetic teeth was obtained after aging at ambient temperature for 24 hours.

EXAMPLE 6

A precursor blend was prepared from the following composition:

| | |
|---|---|
| 24.67% | methyl methacrylate |
| 0.25% | benzoyl peroxide |
| 24.67% | ethylene 'glycol' dimethacrylate |
| 49.70% | poly(methyl methacrylate-co-ethylene dimethacrylate) (99.8:0.2) |
| 0.71% | pigment |
| 100.00% | |

The methyl methacrylate, benzoyl peroxide, and ethylene 'glycol' dimethacrylate were mixed at ambient temperature to form a monomer solution. The polymer and pigment were charged to a planetary dough mixer containing the monomer solution and then mixed until visibly homogeneous. The polymer completely imbibed the monomer solution during the first seven days of contact at ambient tempereature in a sealed container; aging was continued for seven days prior to molding. Monolithic anterior prosthetic teeth were transfer molded by the following sequence:

1. 3 min. at 138° C., 290 psi.
2. 2 min. at 138° C., 1300 psi.
3. 5 min. cool at 1300 psi.
4. 3 hr. at 118° C.

The resultant prosthetic teeth grind with a fine dusty debris, repolish to a high gloss, resist wear, resist methyl methacrylate and other solvents, are hydrolytically stable, show no visible degradation or distortion when heated at 220° C. for one hour, and bond well to denture base material.

AESTHETIC FACING

EXAMPLE 7

A Steele's facing, recognized in the dental industry as a preformed aesthetic veneer which is cemented to the facing and blade of a Steele's coping, was molded from the precursor blend prepared in Example 2. This facing is superior in abrasion resistance to conventional acrylic facings used at present.

ONE-COMPONENT CROWN AND BRIDGE MATERIAL

EXAMPLE 8

The method described in Example 4 was used to prepare the following compositions:

| Step 1 | |
|---|---|
| 53.16% | methyl methacrylate |
| 3.32% | ethylene 'glycol' dimethacrylate |
| 9.97% | 2,2-bis(4-methacryloxyphenyl)propane |
| 0.33% | benzoyl peroxide |
| 33.22% | poly(methyl methacrylate-co-ethylene dimethacrylate) (95:5) |
| 100.00% | |

The crosslinked polymer was in the form of particles, 50% by weight of which were below 100 microns in size, the balance being below about 500 microns in size.

| Step 2 | |
|---|---|
| 37.00% | poly(methyl methacrylate) |
| 49.43% | methyl methacrylate |
| 12.36% | 2,2-bis(4-methacryloxyphenyl)propane |
| 0.31% | benzoyl peroxide |
| 0.90% | pigment |
| 100.00% | |

The poly(methyl methacrylate) had an average molecular weight of 800,000 g/mole. The weight ratio of Step 1 to Step 2 material in this example is 1.50 to 1.00. This gel preparation was identical in utility to that described in Example 4.

The following gel-sols were prepared by shaking vigorously for six hours:

| Gel-Sol 1 | 20.00% | gel formed in Example 7 |
|---|---|---|
| | 80.00% | methyl methacrylate |
| Gel-Sol 2 | 60.00% | gel formed in Example 7 |
| | 40.00% | methyl methacrylate |

A cast nickel-chromium crown and bridge alloy coping made from BIOBOND ™ C&B alloy (trademark of Dentsply International Inc.) was primed by painting with Gel-Sol 1. An opaque primer was also developed by incorporating a higher pigment content, for example, up to 5%, in Step 2 of the gel preparation. While the primer coat was wet, a tooth having the anatomy of an upper central was fashioned on the coping using Gel-Sol 2 which handled like modeling clay. A final coat of Gel-Sol 1 was painted on the formed tooth surface to smooth the surface and act as a glaze. The prepared crown was held in a 43.5° C. (110° F.) air oven overnight; one hour in a 60° C. (140° F.) air oven; and fully polymerized during 1.5 hour immersion in 71° C. (160° F.) water under 1.5 atmospheres of gauged air pressure. The resultant crown was easily buffed to a high gloss using conventional dental acrylic polishing techniques.

The advantages of this material in crown and bridge restorations are that it evidences superior abrasion resistance over conventional acrylic crowns presently used; it is a premixed moldable material which, unlike porcelain crown fabrication, does not require slow build-up techniques; rudimentary, low-cost equipment may be used for its curing compared to high cost ovens necessary for porcelain crown fabrication; and it has excellent polishability after laboratory fabrication and clinical fitting to proper occlusion.

ONE-COMPONENT FILLED CROWN AND BRIDGE MATERIAL

EXAMPLE 9

The composition of Gel-Sol 2, described in Example 8, was extended by adding an inorganic filler:

| 72.00% | Gel-Sol 2, described in Example 8 |
|---|---|
| 28.00% | silane treated micro-fine fumed silica |

The shearing action of a dough mixer was used to disperse the inorganic filler evenly throughout the gel-sol. The procedure detailed in Example 8 was used to form the same type of crown. Gel-Sol 1 of Example 8 was again used as a primer and glaze. The advantages of this filled restoration were the same as cited for the crown obtained in Example 8 except that added abrasion resistance was evidenced.

ONE-COMPONENT DENTURE BASE MATERIAL

EXAMPLE 10

The gel composition, detailed in Example 8, and method of preparation, described in Example 4, was used to prepare a denture base material. An upper denture containing commercial plastic teeth in the left quadrant and commercial porcelain teeth in the right quadrant was prepared using the gel, referred to above, for the denture base. The denture model was cast in wax, invested in stone, and the wax boiled out. The stone was coated with a separator fluid, and trial compression packed with the gel. The gel packed very well and additional packing was not required. The packed case was clamped and immersed in 71° C. (160° F.) water for 12 hours to effect polymerization. Replication of anatomical detail was excellent. The chemical bond to commercial plastic teeth and mechanical retention of commercial porcelain teeth was also excellent. The one-component gel prepared for use as a denture base material in this example was functional and practical after being stored at ambient temperature for 18 months.

ONE-COMPONENT RADIATION CURABLE MATERIAL

EXAMPLE 11

The following gel composition, prepared by the method described in Example 1, was polymerized by ultraviolet radiation having wavelengths of 320 to 400 nanometers using a Caulk NUVA-LITE photo cure unit (registered trademark of Dentsply International) for two minutes:

| | |
|---|---|
| 28.18% | methyl methacrylate |
| 0.45% | 2,2-diethoxyacetophenone |
| 2.01% | 2,2-bis(4-methacryloxyethoxyphenyl)propane |
| 3.36% | ethylene 'glycol' dimethacrylate |
| 43.30% | poly(methyl methacrylate-co-ethylene dimethacrylate) (98.8:1.2) |
| 21.65% | poly(methyl methacrylate) |
| 1.05% | pigment |
| 100.00% | |

EXAMPLE 12

The following gel composition, prepared by the method described in Example 1, was polymerized by visible radiation having wavelengths of 380 to 500 nanometers:

| | |
|---|---|
| 28.23% | methyl methacrylate |
| 0.25% | dimethyl ethanolamine |
| 0.36% | methyl ether of benzoin |
| 0.18% | camphoroquinone |
| 3.32% | ethylene 'glycol' dimethacrylate |
| 1.66% | urethane diacrylate |
| 43.40% | poly(methyl methacrylate-co-ethylene dimethacrylate) (99.6:0.4) |
| 21.70% | poly(methyl methacrylate) |
| 0.90% | pigment |
| 100.00% | |

The compositions described in Examples 11 and 12 are useful for the following exemplary dental material applications:

| | |
|---|---|
| 1. Crown and bridge | 5. Denture reline |
| 2. Crown and bridge repair | 6. Denture repair |
| 3. Temporary filling | 7. Orthodontic splint |
| 4. Crowns of implantable teeth | |

The compositions in Examples 11 and 12 formulated as gel-sols, similar to those described in Example 9, are useful as cavity liners, tooth sealants, restorative primers, and adhesives for orthodontic appliances. Furthermore, the compositions in Examples 11 and 12 have advantages among which are the affording of extended work time, the utilization of premixed polymerizable systems which result in void free structures, the evidencing of long term shelf stability of at least 18 months at ambient temperature, and the requirement of low exotherms for in-the-mouth repairs and restorations.

ONE-COMPONENT FILLED RADIATION CURABLE MATERIAL

EXAMPLE 13

The following gel composition, containing an inorganic filler and prepared by the method described in Example 1, was polymerized by ultra violet radiation having wavelengths of 320 to 400 nanometers using a Caulk NUVA-LITE photo-cure unit (registered trademark of Dentsply International):

| | |
|---|---|
| 21.71% | methyl methacrylate |
| 2.96% | butyl methacrylate |
| 0.27% | 2,2-diethoxyacetophenone |
| 0.43% | 2,2-dimethoxy-2-phenylacetophenone |
| 2.08% | 2,2-bis(4-methacryloxyethoxyphenyl)-propane |
| 1.13% | tetraethylene 'glycol' dimethacrylate |
| 1.13% | neopentyl 'glycol' dimethacrylate |
| 19.95% | poly(methyl methacrylate-co-2,2-bis-(4-methacryloxyphenyl))propane) (99.8:0.2) |
| 12.23% | poly(methyl methacrylate) |
| 37.66% | silane treated, fine (12 micron) particle quartz |
| 0.45% | pigment |
| 100.00% | |

The gel composition disclosed in this example has the same applications as those cited for Examples 11 and 12. In addition, the composition of this example reinforced with the light transmitting quartz filler is useful as a restorative tooth filling material.

STABLE ONE PART DENTAL VENEERS

EXAMPLE 14

A two step preswell process was used to mix a one part dental veneer material. A blend was prepared from the following:

| Step 1 | |
|---|---|
| 2.99% | methyl methacrylate |
| 0.51% | benzoyl peroxide |
| 46.76% | reaction product of hydroxypropyl methacrylate with 2,2,4-trimethylhexyl-1,6-diisocyanate(2:1) (methane urethane dimethacrylate) |
| 49.74% | poly(methyl methacrylate-co-ethylene dimethacrylate) (99.8:0.2) |
| 100.00% | |

The benzoyl peroxide was dissolved in the methyl methacrylate and blended with the urethane dimethacrylate. This solution was then mixed with the poly(methyl methacrylate-co-ethylene dimethacrylate) (99.8:0.2) and stored in the dark in a sealed jar to become the "preswell" blend. The crosslinked polymer was in the form of fine particles at least 50% by weight were below 100 microns in size, and the balance below 500 microns in size. After one month storage the fully swollen crosslinked polymer "preswell" blend was admixed as follows:

| Step 2 | |
|---|---|
| 48.84% | "preswell" blend from Step 1 |
| 51.03% | silane treated microfine silica |
| 0.13% | acrylic acid |
| 100.00% | |

These components were mixed on a three roll mill with minor amounts of pigments as required until a uniformly shaded paste was obtained.

A veneer was prepared on an opaqued crown by the well known build up method. A dentin shade veneer paste was built up on the crown by hand and instrument modelling. Next, an incisor shade veneer paste was built on top of the dentin. The veneer was polymerized by immersion in a 90° C. water bath under three bars air pressure. Veneers were also polymerized by immersion in glycerin in a similar manner. The finished veneer had a high gloss and good esthetic appearance. The veneer has three times the wear resistance of conventional acrylic veneers by a prophy abrasion test. The veneer can be readily shaped by grinding, yielding a dusty debris, and then is readily polished to a smooth, high gloss finish. The veneer is resistant to chemicals and stains, has good impact strength and is repairable. The veneer paste is stable at ambient conditions. Similar composition veneer pastes have been stable for nine months at ambient and seventy days at 50° C.

EXAMPLE 15

A two step preswell process was used to mix a one part dental veneer from the following composition:

| | Step 1 |
|---|---|
| | "Preswell" blend from Example 14 aged 22 days at ambient. |
| | Step 2 |
| 57.29% | "preswell" blend from Step 1 |
| 41.67% | silane treated microfine silica |
| 1.04% | acrylic acid |
| 100.00% | |

The components were mixed on a three roll mill until visually uniform. The putty-like material was formed into a dental veneer and polymerized by immersion in 90° C. glycerin at three bars pressure for ten minutes to yield shapable, durable and aesthetically superior appliances.

EXAMPLE 16

A two step preswell process was used to mix a one part dental veneer from the following composition:

| | Step 1 |
|---|---|
| | "Preswell" blend from Example 14, Step 1, aged three months. |
| | Step 2 |
| 74.96% | "preswell" blend from Step 1 |
| 25.06% | Aluminum Oxide C - Degussa |
| 100.00% | |

The components were mixed on a three roll mill to form a uniform paste. The shaped paste was polymerized at 90° C. and three bars pressure in water for fifteen minutes to yield a hard translucent article.

Examples 14-16 and similar compositions have application as prosthetic teeth denture reline and denture base materials. Similar compositions with suitable light cure initiator, promoters and accelerators have application as tooth filling materials, repair materials for fixed prosthesis and natural teeth. One part mixtures of similar compositions may also be applied in the decorative arts and crafts, auto and boat body repair and to produce molded parts.

It should be understood that while the present invention has been described in considerable detail with respect to certain specific embodiments thereof, it should not be considered limited to such embodiments but may be used in other ways without departure from the spirit of the invention and the scope of the appended claims.

What is claimed is:

1. A hardenable composition comprising a blend of:
   monofunctinal polymerizable monomer,
   di- or polyfunctional crosslinking agent reactive with said polymerizable monomer, and
   from about 10% to about 70% of a crosslinked polymer in the form of discrete particles having average diameters up to about 500 microns,
   said crosslinked polymer particles being sufficiently well crosslinked as to maintain substantially their structural identity when exposed to the monomers component,
   said crosslinked polymer particles being capable of swelling with or imbibing at least 10% by weight of the particles of said monomer component,
   said particles being substantially swollen by said monomer and said crosslinking agent;
   said composition being capable of being hardened into a water insensitive object.

2. The composition of claim 1 wherein said crosslinked polymer is present in an amount of from about 40% to about 60% by weight.

3. The composition of claim 1 wherein said polymerizable monomer is present in an amount of from about 2% to about 5% by weight.

4. The composition of claim 1 wherein said crosslinking agent is present in an amount of from about 40% to about 60% by weight.

5. The composition of claim 1 wherein at least about 50% by weight of said particles have average diameters below about 150 microns.

6. The composition of claim 1 wherein said crosslinked polymer is present in an amount of from about 40% to about 60% by weight, said polymerizable monomer is present in an amount of from about 2% to about 5% by weight, said crosslinking agent is present in an amount of from about 40% to about 60% by weight, and at least about 50% by weight of said particles have average diameters below about 150 microns.

7. The composition of claims 1, 4, 5 or 6 wherein said crosslinking agent is selected from the group consisting of 2,2-bis(methacryloxyphenyl)propane; ethylene "glycol" dimethacrylate; ethylene "glycol" diacrylate; 2,2-bis[4-(2-hydrloxy-propoxy)phenyl] propane; and the reaction product of either hydroxyethyl acrylate, hydroxypropyl acrylate and their methacrylic homologs with 2,2,4-trimethylhexyl-1,6-diisocyanate.

8. The composition of claims 1, 5 or 6 further comprising one or more members selected from the group consisting of free radical initiators, photochemical initiators, activators, pigments, fillers, adhesion modifiers and radiopaquing agents.

9. The composition of claim 8 wherein said blend is admixed with particulate inorganic filler in weight ratios of from about 1:2 to about 2:1.

10. A process for producing a hard, water insensitive, shaped article comprising:
    mixing together a blend comprising:
    monofunctisnal polymerizable monomer,
    di- or polyfunctisnal crosslinking agent reactive with said polymerizable monomer, and from about 10% to about 70% of a crosslinked polymer in the form of discrete particles having average diameters up to about 500 microns, said crosslinked polymer particles being sufficiently well crosslinked as to maintain substantially their structural identity when exposed to the monomer component, said crosslinked polymer particles being capable of swelling with or imbibing at least 10% by weight of the particles of said monomer component, said particles being substantially swollen by said monomer and said crosslinking agent;

said composition being capable of being hardened into said water insensitive object;

maintaining said components in association with one another in said blend for a period of time sufficient to substantially fully swell said particles with mixture of said monomer and said crosslinking agent; shaping said blend; and exposing said blend to heat or to electromagnetic radiation to harden said blend and to provide said shaped article.

11. The process of claim 10 wherein said crosslinked polymer is present in an amount of from about 40% to about 60% by weight.

12. The process of claim 10 wherein said polymerizable monomer is present in an amount of from about 2% to about 5% by weight.

13. The process of claim 10 wherein said crosslinking agent is present in an amount of from about 40% to about 60% by weight.

14. The process of claim 10 wherein at least about 50% by weight of said particles have average diameters below about 150 microns.

15. The process of claim 10 wherein said crosslinked polymer is present in an amount of from about 40% to about 60% by weight, said polymerizable monomer is present in an amount of from about 2% to about 5% by weight, said crosslinking agent is present in an amount of from about 40% to about 60% by weight, and at least about 50% by weight of said particles have average diameters below about 150 microns.

16. The process of claims 10, 13, 14 or 15 wherein said crosslinking agent is selected from the group consisting of 2,2-bis(methacryloxyphenyl)propane; ethylene "glycol" dimethacrylate; ethylene "glycol" diacrylate; 2,2-bis [4-(2-hydroxy-3-methacryloxypropoxy)phenyl]propane; and the reaction product of either hydroxyethyl acrylate, hydroxypropyl acrylate and the methacrylate homologs with 2,2,4-trimethylhexyl-1,6-diisocyanate.

17. The process of claims 10, 14 or 15 further comprising one or more members selected from the group consisting of free radical initiators, photochemical initiators, activators, pigments, fillers, adhesion modifiers and radiopaquing agents.

18. The process of claim 17 wherein said blend is admixed with particulate inorganic filler in weight ratios of from about 1:2 to about 2:1.

19. A dental appliance comprising a hard, water insensitive, shaped body having at least one portion comprising a polymerized blend comprising:

monofunctional polymerizable monomer, di- or polyfunctional crosslinking agent reactive with said polymerizable monomer, and from about 10% to about 70% of a crosslinked polymer in the form of discrete particles having average diameters up to about 500 microns, said crosslinked polymer particles being sufficiently well crosslinked as to maintain substantially their structural identity when exposed to the monomer component, said crosslinked polymer particles being capable of swelling with or imbibing at least 10% by weight of the particles of said monomer component, said particles being substantially swollen by said monomer and said crosslinking agent;

said composition being hardened into said water insensitive shaped body by polymerization.

20. The appliance of claim 19 wherein said crosslinked polymer is present in an amount of from about 40% to about 60% by weight.

21. The appliance of claim 19 wherein said polymerizable nonmer is present in an amount of from about 2% to about 5% by weight.

22. The appliance of claim 19 wherein said crosslinking agent is present in an amount of from about 40% to about 60% by weight.

23. The appliance of claim 19 wherein at least 50% by weight of said particles have average diameters below about 150 microns.

24. The appliance of claim 19 wherein said crosslinked polymer is present in an amount of about 40% to about 60% by weight, said polymerizable monomer is present in an amount of from about 2% to about 5% by weight, said crosslinking agent is present in an amount of from about 40% to about 60% by weight, and at least 50% by weight of said particles have average diameters below about 150 microns.

25. The appliance of claims 19, 22, 23 or 24 wherein said crosslinking agent is selected from the group consisting of 2,2-bis(methacryloxyphenyl)propane; ethylene "glycol" dimethacrylate; ethylene "glycol" diacrylate; 2,2-bis[4-(2-hydroxy-3-methcryloxypropoxy)phenyl]propane; and the reaction product of either hydroxyethyl acrylate, hydroxypropyl acrylate and their methacrylate homologs and 2,2,4-trimethylhexyl-1,6-diisocyanate.

26. The appliance of claims 19, 23 or 24 further comprising one or more members selected from the group consisting of free radical initiators, photochemical initiators, activators, pigments, fillers, adhesion modifiers and radiopaquing agents.

27. The appliance of claim 26 wherein said blend is admixed with particulate inorganic filler in weight ratios of from about 1:2 to about 2:1.

28. The appliance of claim 19, 23 or 24 wherein said appliance exhibits the structure of an interpenetrating polymeric network at least locally interior to said portion.

29. The appliance of claim 27 wherein said appliance exhibits the structure of an interpenetrating polymeric network at least locally interior to said portion.

30. The composition of claim 1 wherein said crosslinking agent is present in an amount of from about 20% to about 70%, and said monofunctional monomer is present in an amount of from about 2% to about 30% to about 30% by weight.

31. The process for claim 10 wherein said crosslinking agent is preset in an amount of from about 20% to about 70%, and said monofunctional monomer is present in an amount of from about 2% to about 30% by weight.

32. The appliance of claim 19 wherein said crosslinking agent is preset in an amount of from about 20% to about 70%, and said monofunctional monomer is present in an amount of from about 2% to about 30% by weight.

* * * * *